(12) United States Patent
Farquharson et al.

(10) Patent No.: US 8,781,757 B2
(45) Date of Patent: Jul. 15, 2014

(54) METHOD AND APPARATUS FOR DETERMINING PROPERTIES OF FUELS

(75) Inventors: Stuart Farquharson, Meriden, CT (US); Wayne W. Smith, South Glastonbury, CT (US)

(73) Assignee: Real-Time Analyzers, Inc., Middletown, CT (US)

( * ) Notice: Subject to any disclaimer, the term of this patent is extended or adjusted under 35 U.S.C. 154(b) by 342 days.

(21) Appl. No.: 12/734,091

(22) PCT Filed: Oct. 10, 2008

(86) PCT No.: PCT/US2008/011668
§ 371 (c)(1),
(2), (4) Date: Apr. 9, 2010

(87) PCT Pub. No.: WO2009/082418
PCT Pub. Date: Jul. 2, 2009

(65) Prior Publication Data
US 2010/0211329 A1    Aug. 19, 2010

Related U.S. Application Data

(60) Provisional application No. 60/998,627, filed on Oct. 12, 2007.

(51) Int. Cl.
*G06F 19/00* (2011.01)

(52) U.S. Cl.
USPC ................................. 702/28; 702/30

(58) Field of Classification Search
USPC .................................... 702/28, 30
See application file for complete search history.

(56) References Cited

U.S. PATENT DOCUMENTS

| | | | |
|---|---|---|---|
| 4,963,745 A | 10/1990 | Maggard | |
| 5,139,334 A | 8/1992 | Clarke | |
| 5,349,188 A | 9/1994 | Maggard | |
| 5,999,255 A * | 12/1999 | Dupee et al. | 356/301 |
| 6,897,071 B2 * | 5/2005 | Sonbul | 436/171 |
| 7,842,264 B2 * | 11/2010 | Cooper et al. | 423/210 |
| 2006/0053005 A1 * | 3/2006 | Gulati | 704/226 |
| 2006/0283931 A1 * | 12/2006 | Polli et al. | 235/375 |
| 2007/0143037 A1 * | 6/2007 | Lundstedt et al. | 702/30 |

* cited by examiner

*Primary Examiner* — Michael Nghiem
*Assistant Examiner* — Alexander Satanovsky
(74) *Attorney, Agent, or Firm* — Ira S. Dorman

(57) ABSTRACT

The method and apparatus are used to determine class, grade and properties of fuel samples, regardless of ambient, instrument, or sample temperature, using mathematical correlations between fuel class, grade and properties and their spectra developed from a database of samples with measured properties and spectra. The ability to measure a fuel sample using the present method and apparatus is useful in identifying unknown fuel samples, determining suitability in equipment, and monitoring and controlling fuel processes, such as blending operations, distillation, and synthesis.

17 Claims, 7 Drawing Sheets

METHOD AND APPARATUS FOR DETERMINING PROPERTIES OF FUELS

CROSS-REFERENCE TO RELATED APPLICATION

This application claims the benefit of U.S. Provisional Patent Application No. 60/998,627 filed Oct. 12, 2007, the entire specification of which is incorporated hereinto by reference thereto.

STATEMENT OF GOVERNMENT INTEREST

This invention was made with Government support under Contract No. M67854-03-C-5043, awarded by the U.S. Marine Corps. The Government has certain rights in the invention.

BACKGROUND OF THE INVENTION

The present invention relates to methods and apparatus to determine chemical, chemical-based and physical properties of hydrocarbon fuels, which are derived or synthesized from petroleum or biomass (e.g. gasoline and biodiesel, respectively).

The applications of the various classes of hydrocarbon fuels are based on their chemical, chemical-based and physical properties. In the case of gasoline, aromatic content, a chemical property, and octane number, a chemical-based property, are among the properties that are important to engine performance; for diesel fuels, cetane index is an example of chemical-based property important to performance; while for jet fuels, freeze point, flash point and viscosity are important physical properties. All properties are ultimately due to the chemical composition of each fuel, which is largely determined by the temperature range at which the fuels are collected during distillation of crude oil. The composition of the crude oil, the refinery and distillation system used, also influence the fuel composition. The properties of these fuels are typically measured using numerous chemical and physical property analyzers to classify the fuel and certify that property specifications are met for commercial use. These certified measurements are known as American Society for Testing and Materials (ASTM) methods. For example, aromatic content is determined by gas chromatography according to ASTM D1319, while flash point, the temperature at which a sample ignites, is determined by a closed-cup tester according to ASTM D93. These methods generally require 30 minutes or more to perform, are labor intensive, require controlled laboratory conditions, and are subject to human error. For example, in determining flash point according to ASTM D93, the operator must apply uniform heating and mixing to the sample, control the heating rate, create a spark above the liquid, and read the temperature when the fuel ignites from a thermometer or a thermocouple digital display (that may have different ° F. or ° C. gradiations). According to the ASTM Subcommittee (ASTM D93 "Standard Test Methods for Flash Point by Pensky-Martens Closed Cup Tester", D02.08.0B, 2006), flash point measurements are reproducible to a standard deviation of 5.8° C. for diesel and 4.3° C. for jet fuel samples (approximately 8.5% of the value in either case).

However, fuel specifications vary internationally, and may not meet the requirements for a particular vehicle in foreign service, such as the use of military vehicles overseas, and consequently the fuel needs to be qualified prior to use to ensure proper vehicle performance. This qualification typically includes classifying the fuel as gasoline, diesel, or jet, and determining the chemical, chemical-based, and physical properties as required for each class. Biodiesel has its own specifications, and due to the fact that there is considerable difference in the starting materials (animal fat, corn oil, fish oil, spent vegetable oil, etc.), fuel quality is even a greater issue.

Furthermore, the method and apparatus used to characterize the fuel should take into account the ambient and fuel temperature to obtain the most meaningful results, and should be sufficiently rugged to perform measurements on-site, such as at a distribution center or even a refinery. It is also preferable that the analysis be performed quickly and without sample pretreatment. These latter suggested capabilities, along with the ability to integrate into processing equipment, would also allow monitoring the separation of fuels in refining and distillation apparatus, the synthesis of biofuels in reactors, or blending of fuels in mixers. Furthermore, the ability to monitor properties in the process would allow controlling the process conditions that influence those properties, such as the temperature of a distillation column.

The apparati most capable of fulfilling these requirements are spectrometers, such as ultraviolet, visible, fluorescence, near infrared, infrared, and Raman spectrometers. This patent application describes the use of a portable Raman analyzer, at locations not restricted to chemical laboratories, to determine fuel class, grade and properties. The analyzer measures the Raman spectrum of the fuel and employs a spectral database to correlate the spectrum to the fuel class, grade and properties.

The primary use of Raman spectroscopy in industry is to quantify each chemical component in a chemical mixture. In the case of fuels, the shear number of components making up a typical petroleum fuel, on the order of several hundred (see for example Uhler et al., Molecular fingerprinting of gasoline by a modified EPA 8260 gas chromatography/mass spectrometry method, *Int. J. Environ. Anal. Chem.* 83, 1-20, 2003), makes the identification and quantitation of each chemical component impossible. However, several research groups have shown that qualitative chemical analysis, such as the general composition of fuel, can be determined from Raman spectra.

Kalasinsky et al. teach that Raman spectroscopy can be used to determine general hydrocarbon composition of kerosenes, specifically that the aromatic, alkane and alkene hydrocarbons are strongly associated with Raman peaks at 990-1010 $cm^{-1}$, ~1050 $cm^{-1}$, and 1550-1700 $cm^{-1}$, respectively (Quantitative Analysis of Kerosenes by Raman Spectroscopy," *Energy & Fuels,* 3, 304-307, 1989). In a similar fashion, Chung et al. showed that Raman spectroscopy could be used to determine relative aromatic content in jet fuels by comparing the phenyl and biphenyl ring stretching modes at ~1007 and 1386 $cm^{-1}$ to the alkane $CH_2$ wagging mode at 1450 to 1475 $cm^{-1}$ (Analysis of Aviation Turbine Fuel Composition by Laser Raman Spectroscopy," *Appl. Spec.,* 45, 1527-1532, 1991).

In U.S. Pat. No. 5,139,334 Clark et al. (Hydrocarbon analysis based on low resolution Raman spectral analysis, 1992) teach the use of ratios of aromatic and alkane Raman peaks to predict pump octane number (PON), which, just as motor octane number and research octane number (MON and RON), is related to these chemical components. In one embodiment they use the ratio of the aromatic peak at ~1006 $cm^{-1}$ to the alkane peak at ~1450 $cm^{-1}$ to calculate PON. They show that the PON increases as the ratio of the aromatic peak intensity divided by the alkane peak intensity increases. This is easily understood by examining the octane rating for the primary chemicals of gasoline. It is composed of alkanes (paraffins), alkenes (olefins), cycloalkanes (naphthenes), and aromatics (primarily benzene, ethylbenzene, toluene and xylenes, known collectively as BTEX). The Raman peak at 1450 cm$^{-1}$ is mostly due to the CH$_2$ wagging mode of straight chain alkanes, which have very low octane ratings. In fact, n-octane has a zero octane value and is used to define the low end of the octane scale. Gasoline can contain as much as 80% alkanes. The Raman peak at 1006 cm$^{-1}$ is primarily due to toluene, but benzene, ethylbenzene and meta-xylene also produce intense peaks close to this wavenumber. These single ring aromatics have octane ratings well over 100 (see for example Modern Petroleum Technology; 5th Edition Part II; Edited by G. D Hobson, Wiley 1984, page 786), and are often added, up to the regulated limit of 35%, to increase the octane rating of gasoline as part of the blending process (for example see Muller, New method produces accurate octane blending values, Oil & Gas Journal, 23, 80-90, 1992). Consequently one would expect that a gasoline with a PON of 94 will have a higher 1006 cm$^{-1}$ to 1450 cm$^{-1}$ ratio than a gasoline with a PON of 86. It is not surprising that a ratio of the integrated area under the 200 to 2000 cm$^{-1}$ spectral region to the 2000 to 3500 cm$^{-1}$ spectral region produces a similar trend, since the lower region is dominated by the aromatic contributions, while the higher region is dominated by alkane contributions (CH$_2$ and CH$_3$ stretching modes).

The vapor pressure of a gasoline indicates the ease at which it can be combusted. It is typically measured at 100° F. and reported as the Reid vapor pressure (RVP). The RVP of gasoline is dominated by the lower molecular weight fractions, butanes and pentanes, and is regulated at near 9 psi. It is often adjusted by the addition of n-butane, which has an RVP of 51.6 psi. Although the RVP could be viewed as a physical property of gasoline, it in fact largely depends on the amount of n-butane. And just like determining octane numbers by measuring aromatic content, RVP can be determined by measuring n-butane content based on the intensity of its unique Raman C-C stretching mode at ~830 cm$^{-1}$.

Improvements in calculating both the octane (MON, RON and PON) and Reid vapor pressure values can be obtained by including more Raman spectral features and weighting their contributions to the property of interest in the form of a linear or non-linear combination of features. This mathematical approach coupled with statistical treatment of the chemical data (spectra and property values) is generally referred to as chemometrics. The use of chemometrics to improve correlations between Raman spectra and fuel properties is taught by Cooper et al. in U.S. Pat. No. 5,892,228 (Process and apparatus for octane numbers and Reid vapor pressure by Raman spectroscopy, 1999). A linear regression model, partial least squares (PLS), was used to correlate various parts of the Raman spectra to these properties. In essence Cooper added more Raman spectral features to those employed by Clark to improve the accuracy of the predicted values. This required measuring the Raman spectra of several hundred fuel samples with known octane and vapor pressure values to establish a statistical basis for the correlations.

In a similar manner, Williams et al. used chemometrics to establish a relationship between cetane values (index and number) and Raman spectra for some 18 diesel samples ("Determination of Gas Oil Cetane Number and Cetane Index Using Near-Infrared Fourier Transform Raman Spectroscopy,"Anal. Chem., 62, 2553-2556, 1990). Again, the success of this approach can be explained by the fact that the cetane number is defined by the relative proportions of n-hexadecane (cetane) and alpha-methylnaphthalene. These researchers also show that various principal components of correlation (one positive, one negative) look nearly identical to the Raman spectra for these two chemicals. In fact, it is clear that a ratio of the 1378 cm$^{-1}$ naphthalene Raman peak to the 1445 cetane CH$_2$ wag could be correlated to the cetane number of these diesel samples.

In the case of determining the chemical composition of fuels and developing correlations, there are two limitations associated with most commercial Raman analyzers and all portable Raman analyzers. First, they employ excitation lasers that use visible wavelengths, which generate fluorescence in many fuels, especially diesels. This fluorescence often obscures the Raman spectrum, which in turn eliminates the possibility of determinating chemical composition or developing property correlations. However, the availability of near-infrared wavelength lasers, the most common being neodymium-based lasers that emit at 1064 nm, allows overcoming this difficulty, as they rarely generate fluorescence in the sample. Second, these analyzers use array-based detectors, which can not maintain x-axis stability or reproducibility. Changes in ambient temperature cause distortions in the optics that are used to separate the Raman spectrum into its component wavelengths, usually gratings. For example, an increase in temperature will expand the grating causing the spectrum to expand across the detector in an accordion fashion. Furthermore, the conversion efficiency of photons to electrons for each detector element in the array is slightly different. And, the charge generated in each element can "bleed" to adjacent elements, and the amount of this bleeding changes with the amount of photons hitting the detector element. Consequently, the spectral response for one array of detector elements is different from another and changes with measurement conditions (e.g. the temperature and the intensity of the Raman spectrum measured). Bowie, et al. measured and reported these limitations in ("Factors affecting the performance of bench-top Raman spectrometers."Appl. Spec, 54, 164A-173A, 2000). Unfortunately, successful use of chemometric models requires absolute stability and reproducibility in the x-axis.

It is worth stating that similar correlations between near-infrared (NIR) spectroscopy and gasoline properties have also been developed. Kelly et al. showed that the major components of gasoline could be determined by NIR ("Nondestructive Analytical Procedure for Simultaneous Estimation of the Major Classes of Hydrocarbon Constituents of Finished Gasolines,"Anal. Chem., 62, 1444-1451, 1990), and that this information could be used to predict octane numbers ("Prediction of gasoline octane numbers from near-infrared spectral features in the range of 660-1215 nm", Anal. Chem. 61, 313-320, 1989). Patents granted to Maggard disclose these ideas (U.S. Pat. No. 4,963,745, "Octane measuring process and device", 1990, and U.S. Pat. No. 5,349,188, "Near infrared analysis of PIANO constituents and octane number of hydrocarbons", 1994, where PIANO stands for paraffin, isoparaffin, aromatic, napthenes and olefins).

It is clear from the forgoing that the correlations between Raman spectra and fuel properties, specifically octane, cetane and vapor values, are based on identifiable chemical composition, in this case, phenyl, biphenyl and butane content, respectively. Such properties are defined herein as chemical-based properties. The foregoing does not teach the use of chemometrics applied to Raman or NIR spectra to determine other important fuel properties such as physical state changes (e.g. freezing and boiling point), heat of combustion, lubricity, thermal stability or viscosity. Nor does the foregoing teach the use of chemometrics to compensate for temperature changes in the sample, instrument, or the ambient environment. Nor does the foregoing teach the use of chemometrics to transfer the correlation model from one spectrometer to another. Nor does the forgoing teach the use of chemometrics to distinguish one class of fuel from another, such as gasoline versus diesel versus jet fuel, or distinguish grade of fuel within a class, such as Jet A from Jet A 1 from JP-5, etc. Nor does the forgoing teach the use of Raman-based chemometric models to control fuel class, grade or properties during distillation of petroleum at refineries, or control yield in a biodiesel reactor. Nor does the foregoing teach the use of chemometrics to identify the class or grade of an unknown fuel. Nor does the foregoing teach the use of a coarse model to identify unknown fuels by class and a refined model to better predict its properties. Nor does the foregoing teach the use of a model to identify fuel by grade and a further reined model to better predict its properties. Nor does the foregoing teach the use of refined models that correct for temperature, x- and y-axis variations, modified or mixed fuels to better predict properties.

SUMMARY OF INVENTION

It is a broad object of the present invention to provide a novel method and apparatus to determine properties of a given hydrocarbon fuel sample from a spectrum measured in or out of a laboratory by using a model consisting of one or more weighted spectral regions created from a database of measured spectra and properties for fuel samples that establishes the required correlations between the spectra and the sample fuel properties.

It is another broad object of the present invention to determine fuel class of a measured fuel sample. As used herein, the word "fuel class" means biodiesel, diesel, gasoline, and jet fuel. Furthermore, jet fuel is taken to be synonymous with aviation fuel.

It is a further object of the present invention to determine fuel grade within a class. Specific examples include high-test gasoline, Diesel 1 and Diesel 2, Jet A, Jet A 1, JP-5, and the like.

An additional object of the present invention is to determine modified fuels. Examples include aviation gasoline (AVGAS is gasoline with high octane additives, such as isooctane or tetraethyl lead), blended biodiesel (e.g. Biodiesel 20 is an 80/20 v/v ratio of petroleum diesel and biodiesel), JP-4 (also known as Jet B, a mixture of gasoline and jet fuel), JP-8 (Jet A or Jet A1 plus military specified additives), oxygenated fuel (e.g. gasoline plus methyl tertiary butyl ether, MTBE), reformate (catalytically prepared highly-branched hydrocarbons with high-octane values), and other modified fuels commonly used in engines and motors.

Yet another broad object of the present invention is to provide a novel method and apparatus to determine fuel properties of a given sample, wherein these properties are chemical properties, chemically-based properties, or physical properties. Herein chemical properties include, but are not limited to acid, alcohol, aldehyde, alkane, alkene, aromatic, base, biphenyl, ester, ether, glycol, naphthene, phenyl, sulfur, triglyceride, and water. Chemical-based properties are properties that are due to specific chemicals or chemical functional groups, such as those that can be identified in the sample based on a spectrum, such as a Raman spectrum. These include, but are not limited to, octane numbers (MON, RON and PON), cetane number and Reid vapor pressure. Physical properties are properties that can not be determined from specific chemicals or chemical functional groups, but are instead due to the collective dependent and independent properties of all of the chemicals present. Examples include, but are not limited to boiling point, cloud point, distillation points (e.g., initial distillation temperature, 10, 20, 30, 40, 50, 60, 70, 80, and 90 percent distillation temperatures, and final distillation temperature), flash point, freezing point, pour point, lubricity, density, net heat of combustion, thermal stability, and viscosity.

It is a more specific object of the invention to develop a spectral database used in models to correlate fuel spectra to fuel properties using a spectrometer, especially a Raman spectrometer.

It has now been found that certain of the foregoing and related objects of the invention are achieved by the provision of a method for determining spectroscopically the value of at least one property of a fuel sample of unknown character, comprising:

providing a coarse mathematical model, created using a database, in which either or both of (a) the nature and values of characteristics that are indicative of fuels of at least one class, or (b) one or more spectral representations of such characteristics, taken cumulatively, at temperatures over a range of common values, are correlated to measured spectra in a selected spectral range, such fuel characteristics including, directly or indirectly, chemical functional groups and a plurality of properties (i.e., chemical, chemical-based, and physical properties);

providing a multiplicity of fine mathematical models, created using the database, in each of which a plurality of spectral components are correlated to a property of fuels within the "at least one class," and at temperatures over the range of common values referred to, such correlations being based upon either or both of (a) the nature and value of fuel characteristics, or (b) one or more spectral representations of such characteristics, taken cumulatively, separate pluralities of the multiplicity of fine mathematical models being grouped together so as to provide a multiplicity of fine model groups, a first plurality of such fine model groups being peculiar to fuels within the "at least one class";

obtaining a spectrum, within the spectral range referred to, of a fuel sample of unknown character, at least at one temperature within the range of common values;

performing a coarse analysis of the obtained spectrum by comparing the obtained spectrum to the measured spectra, using the coarse mathematical model, so as to identify a class to which the fuel of the sample belongs; and performing a fine analysis of the obtained spectrum, if the class to which the fuel of the sample belongs is the "at least one class," by comparing the obtained spectrum to the measured spectra, using the plurality of fine model groups peculiar to fuels within the "at least one class," so as to thereby determine a value for the correlated property of the fuel of the sample.

Each of the mathematical models employed in the present method will normally comprise at least one weighted spectral region created from the database, and the spectral representations comprising the coarse model may include an average of spectra within the "one fuel class," an average of spectra within one fuel grade, an average of first derivatives of spectra within the one fuel class, an average of first derivatives of spectra within one fuel grade, a regression model from which the spectra within the one fuel class are produced, or a regression model from which the spectra within one fuel grade are produced.

The nature and values of the fuel characteristics that are indicative of fuels of at least a second class (i.e., a second, third, fourth, or more classes), at temperatures over the range of common values, may also be correlated, in the coarse model, to measured spectra in the selected range, in which case a second plurality (and a third plurality, a fourth plurality, etc.) of the fine model groups will be peculiar to fuels in the second (third, fourth, etc.) class, and the fine analysis of the obtained spectrum will be performed if the class to which the sample belongs is either the at least one class or the second class (or the third, fourth, etc. class as the case may be). Needless to say if a fuel belongs to a second class, a third class, or a fourth class, the model groups peculiar to that class will be used to perform the fine analysis.

Thus, characteristics that are indicative of fuels of a variety of classes are so correlated, in the coarse model, to the measured spectra, with the variety of classes including, more particularly, gasolines, diesel fuels, biodiesel fuels, and aviation fuels. The grades of the fuels of within such classes may include, for example, gasoline octane grades, oxygenated gasolines, diesel 1, diesel 2, Jet A, Jet A1, JP-4, JP-5, JP-7, JP-8, biodiesel 20, biodiesel 50, and biodiesel 100.

The chemical properties to which the measured spectra may be correlated in the coarse mathematic model employed in the present method include, for example, acid, alcohol, aldehyde, alkane, alkene, aromatic, base, biphenyl, ester, ether, glycol, naphthene, phenyl, sulfur, triglyceride, and water. The chemical-based properties may include octane number, cetane number, and Reid vapor pressure, and the physical properties may include flash point, viscosity, density, net heat of combustion, cloud point, pour point, boiling point, freezing point, lubricity, thermal stability, and initial, final, and intermediate distillation temperatures.

The database from which the mathematical models employed in the present method are created will usually be constructed by measurement of at least about 100 different fuels (and preferably substantially more). Sample temperatures and/or instrument temperatures and/or ambient temperatures may be employed in creating the models, and normally the temperatures will be in a range of values from −32° to 52° Centigrade; the measured spectra will desirably be measured at temperature increments of no greater than about 20 Centigrade degrees. The spectra obtained will preferably be Raman, infrared, or near-infrared spectra, and in certain instances the x-axis of the obtained spectrum will adjusted so as to cause the major spectral peaks to substantially match the major peaks of spectra in the database; other spectral adjustments may also be desirable.

Other objects of the invention are attained by the provision of apparatus for determining, spectroscopically, the properties of a fuel sample of unknown character, comprising an analyzer and transmission means for providing, to the analyzer, spectral data obtained from a fuel sample. Broadly defined, the analyzer of the apparatus includes means providing a coarse mathematical model, means providing a multiplicity of fine mathematical models, means for performing a coarse analysis of an obtained spectrum, and means for performing a fine analysis of the obtained spectrum, all as hereinabove and hereinafter described. The analyzer will usually comprise a Raman, an infrared, or a near-infrared spectrometer, and it will preferably be portable. Normally, the apparatus will additionally include temperature-measuring means (typically a thermocouple, a thermometer, a thermister, a pyrometer, or a combination of such devices) for determining ambient temperature (at least).

Further objects of the invention are attained by the provision of a method for monitoring and controlling activity involving a fuel composition, so as to satisfy at least one selected criterion. The method will employ a coarse mathematical model and a multiplicity of fine mathematical models, and will involve the steps of obtaining a spectrum, performing a coarse analysis of the obtained spectrum, and performing a fine analysis of the obtained spectrum, all as hereinabove and hereinafter described. The activity monitored and controlled may for example entail the processing of a fuel composition, wherein the applicable criterion may relate to the chemistry and/or the properties of the fuel composition. Alternatively, when the fuel composition comprises a mixture of at least two different fuels the activity may be carried out so as to separate at least one of the fuels from another, again with the criterion applied relating to the chemistry and/or the properties of at least one fuel of the fuels. The activity may also comprise blending of at least two different fuels, it may comprise synthesizing a biodiesel fuel from at least two chemicals in a reactor, it may comprise identifying a contaminant in the fuel composition, it may comprise a determination as to whether the properties of a fuel comprising the fuel composition are within predefined limits, and it may comprise the control of a manufacturing process.

The spectral database provided in accordance with the invention consists of spectra collected from a series of fuels with known properties, which have been measured at several ambient and sample temperatures and on several spectrometers of the same type, so that once developed the model can be used to determine the same fuel properties on new samples, regardless of the ambient or sample temperature or the spectrometer used. These models then allow analyzing samples over a broad temperature range that may be experienced outside of mobile or building laboratories, which are typically controlled at temperatures close to 25° C. (e.g. 20-30° C.). This includes the use of the model to accurately determine class, grade, and properties of unknown fuels, and utilization of such information to allocate use in equipment and vehicles, or identify adulterated, contaminated and sabotaged fuels. This also includes the use of the model to accurately monitor fuel properties in petrochemical plants for the purpose of blending fuels, controlling fuel class and grade, change-over of fuel classes or grades in pipelines, distillation, fractionation, reforming processes, or fuel synthesis in reactors (such as used to make biodiesel). Examples of blending operations include controlling the relative feed rates of two gasolines having different octane ratings to produce a gasoline with a specific octane rating, controlling the amount of oxygenates, such as methanol, ethanol, or MTBE, etc., added to gasolines to achieve a desired weight percent oxygen (~2-3 wt %), or controlling the amount of biodiesel added to petroleum diesel to make diesel 20. The reforming process is the catalytic driven conversion of low octane naphthas into high octane fuels, known as reformates, which are added to gasolines.

Models used in the method of the present invention to develop correlations between spectra and fuel properties are based on one or more statistically supported mathematical relationships between the measured spectra of a series of fuels and their known properties. This mathematical relationship will normally be a regression model that correlates one or more spectral regions from the spectra of the series of measured fuels to their previously measured or otherwise known properties. In the case of chemical and chemical-based properties, these regions usually correspond to Raman spectral peaks.

The regression model can range from a simple series of weighted terms, such as weighted spectral regions, that correlate to the fuel property or properties, to a complex mathematical relationship that employs higher order terms and includes other variables, such as the ambient and sample temperatures, other spectroscopic properties (such as a fluorescence contribution to a Raman spectrum), or an instrument spectral response function.

The regression model will normally be a linear regression model, such as principal component analysis, principal component regression analysis, partial least squares, classical least squares, inverse least squares, or any of a number of models used to develop chemometric relationships.

These models also preferably employ one or more spectral pre-treatment (preprocessing) steps to normalize the spectral intensity of all spectra in the correlation data set and the measured sample prior to mathematical analysis. Such preprocessing steps include baseline corrections, such as setting the baseline to zero (offset), removing tilt in the baseline, fitting the baseline with polynomial or exponential equations then subtracting the fit from the spectrum, or taking the first, second, or higher-order derivatives of the spectrum. Another form of baseline and offset corrections, multiplicative scatter corrections, employs the entire spectral data set to determine average values for such corrections, which are then applied to a measured spectrum prior to chemometric treatment. For this type of correction it is best to employ regions of the spectrum that do not contain chemical information. The 2000 to 2600 $cm^{-1}$ spectral region is usually suitable when the database consists of Raman spectra.

Preprocessing also includes normalization of the spectral intensity. This includes range normalization, such as setting the baseline to zero and the most intense peak to 1, and other common normalization methods, such as mean-centered and maximum normalization. Mathematical methods, such as a moving average, Savitsky-Golay, etc., may also be used to smooth the spectra to reduce the noise. For example, the former preprocessing method replaces the intensity value of each spectral resolution element with the average of the intensity for a user-specified set of spectral resolution elements on either side of the value being replaced.

These models can also be used to group fuels by class or grade based on the spectral uniqueness of the fuel class or grade. For example, each group can be defined in terms of a unique principal component that is common to the fuels within the group, but distinct from all other groups. A value representing how well a member of a group belongs to that group can be generated by subtracting the principal components of that member from the principal components that define the uniqueness of the group. Such PCA distances are often calculated using more sophisticated means than simple subtraction, known as distance algorithms, such as Absolute Value, Correlation, Euclidean, Least Squares, Mahalanobis distance algorithms, etc. Typically, a statistical confidence level is used, such as 95%, to determine if a value is likely a member of a group. In this way a model can be used to determine from the measured spectrum of an unknown sample if it belongs to a group, i.e. identify its fuel class and grade, or determine that it does not belonging to any fuel class or grade and is therefore an outlier. Such a model could also compare the PC distance values of an unknown sample to the PC representing each fuel class and grade to identify and quantify fuel mixtures.

The model preferably has provision to input the spectral response function of the spectrometer used, the ambient temperature, and the sample temperature so that appropriate corrections can be made. Herein the spectral response function is defined as the measured intensity (Y-axis) for the spectrometer, including the entire optical train, detector, and electronics, as a function of wavenumber (X-axis) in response to a broad band light source, such as a white light or black body radiating source.

In the case of using Raman spectroscopy to build the spectral database and measure samples, the model preferably has provision to input the laser excitation wavelength value used to measure the sample and shift the spectra as appropriate to coincide to that of spectra collected with the laser excitation wavelength used to build the model. In the case of using interferometer-based Raman spectrometers, the model preferably has similar correction capability for the clocking laser. The model preferably also has provision to use the position of a Raman peak that is invariant to fuel properties, such as the $CH_2$ wag at 1450 $cm^{-1}$, to correct x-axis shifts in the Raman spectra due to laser wavelength shifts. These capabilities separately or together allow using the model on different spectrometers of the same type, such as two interferometer-based Raman spectrometers.

The model can be used to monitor, control, and even predict fuel properties using measured Raman spectra in process streams, reactors, or the like. Examples include monitoring gasoline during blending operations to achieve a desired octane rating, or monitoring reaction rates, controlling yield, and predicting fuel properties, such as viscosity in a biodiesel reactor. The model and measured Raman spectra can be used to determine chemical composition and predict properties in a distillation tower so that the fuel class and grade fraction being boiled and collected, can be selected. For example, the process can be controlled to select between diesel and jet fuel, or even between Jet A and JP-5. Fiber optic coupled probes could be used to allow measurements inside such processing apparatus so that measurements can be effectively real-time, such as every minute, and allow timely process control.

Spectrometers used to measure such fuel samples for the purpose of developing such spectral databases used in models to correlate fuel spectra to fuel properties will normally include fluorescence, laser induced breakdown, ultraviolet, visible, infrared, near infrared, Raman and terahertz spectrometers. For convenience, much of the disclosure that follows is specific to Raman spectroscopy, but that should not be taken as limiting the scope of the invention.

A Raman spectrometer may use a dispersive device, such as a grating, to separate the Raman spectra into their components wavelengths and display them on an array detector, such as a charge-coupled device, or more preferably the Raman spectrometer uses an interferometer to separate the Raman spectra into their component wavelengths as a function of mirror displacement and display them on a single element detector during the course of a timed scan. The spectrometer is preferably portable, most desirably weighing less than 50 pounds. It is preferably capable of operating effectively in industrial (or other) settings that include ambient vibrations, such as may be generated by motors and pumps, and at outdoor temperatures; i.e., the spectrometer will most desirably be able to operate at any temperature from −25 to +125° F. (−32 to +52° C.).

A Raman spectrometer will include transmission means, such as an optical interface to the sample, so that the excitation laser can be directed into the sample and the scattered Raman energy can be collected. The optical interface preferably is a focusing lens, or a focusing lens in combination with an optical window. The optical interface may be incorporated into a sample compartment or a fiber optic coupled probe. Preferably, the sample compartment can hold sample containers such as capillaries, cups, pipettes, test tubes, vials, or the like.

Preferably the sample holder or probe contains a means of determining the sample temperature. Such means includes pyrometers, thermistors, thermometers, thermocouples, etc. that can measure and transmit temperature.

The fiber optic coupled probe can preferably be in intimate contact with the fuel being measured. Such a probe may be at the end of a pole or cable so that measurement can be performed in a vehicle or storage fuel tank. Such a probe may be interfaced into a fuel pipe line, a fuel distillation column, a petroleum fractionation tower, or apparatus used in blending, reforming or oxygenating fuels, or synthesizing fuels, such as apparatus used to convert animal fat and vegetable oil feedstocks into biodiesel. Such feedstocks include, chicken fat, fish oil, olive oil, vegetable oil, and the like.

The Raman spectrometer will in most cases use a laser that emits energy at a wavelength from the ultraviolet to the near infrared portion of the spectrum to generate the Raman signal in fuel samples. The laser wavelength is preferably longer in wavelength than 750 nm, more preferably between 950 and 1500 nm, and most preferably 1064 nm.

The Raman spectrometer preferably has provision to determine the following operational parameters: the laser excitation wavelength, the clocking laser wavelength for interferometer-based Raman spectrometers, the spectral response function, the ambient temperature, the instrument temperature, and the sample temperature.

DETAILED DESCRIPTION OF THE PREFERRED EMBODIMENTS

As indicated above, the present invention provides novel apparatus and methods to determine fuel properties at different ambient and sample temperatures using more than one instrument or analyzer of the same type. Illustrative of the efficacy of the present invention are the following examples:

Example One

Figure 1:
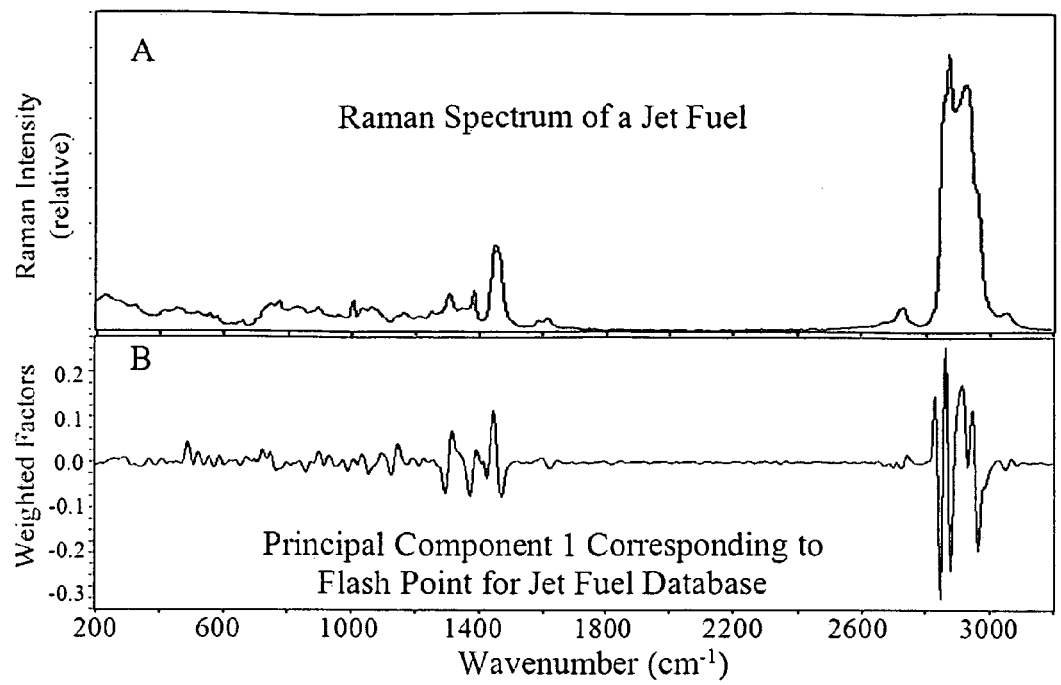
FIG. 1 is a plot of curves comparing the A) Raman spectra of one of the jet fuels used to build the model to B) the Principal Component 1 correlating Raman spectra to flash point for the entire database. Principal Component 1 illustrates both positive and negative correlations between the spectra and flash point values and the weighted factors that should be applied to predict flash point for an unknown sample.

The flash points of 320 jet fuels were measured manually by numerous people at several laboratories according to the ASTM D93 method, discussed above, which at best is reproducible to a standard deviation of 4.3° C. These 320 samples were placed in 2 mL glass vials and their Raman spectra were measured using a portable FT-Raman spectrometer employing 0.5 W of 1064 nm excitation laser power, 8 $cm^{-1}$ resolution and a 60 second accumulation time. A typical Raman spectrum is shown in FIG. 1A.

A correlation model between the measured Raman spectra and flash points was initially developed by first examining the entire spectrum (200 to 3200 $cm^{-1}$) to determine the regions that correlated most to the flash point values. Principal Component 1 showed that weighted factors, both positive and negative, in the regions from 700 to 1700 $cm^{-1}$ and 2700 to 3100 $cm^{-1}$ provided the greatest correspondence (FIG. 1B). The model was then refined by using just these spectral regions, as well as three additional Principal Components, to produce the correlation shown in FIG. 2 for the flash point measured values by ASTM methods plotted versus the predicted values from the Raman spectra (open squares). A perfect correlation would yield a one-to-one match between measured and predicted values with no error (no scatter) in either set of values. A 45° line representing a perfect correlation is included in the figure for comparison. There is in fact scatter in the data, and the error for a linear least squared fit to the data, $R^2$, is 0.74 (1.0 is a perfect fit), and a standard error of prediction is calculated to be 2.75° C. for the data set.

Figure 2:
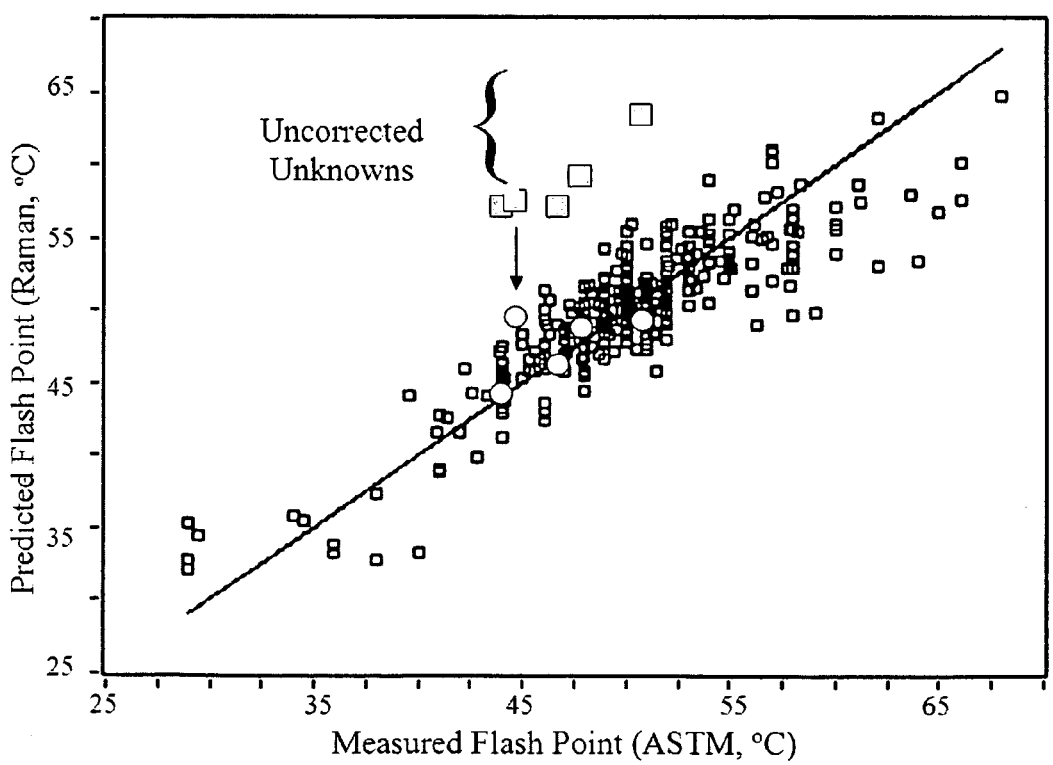
FIG. 2 is a plot of measured versus predicted flash point values for 320 jet fuels (open squares). The measured values were obtained by standard ASTM methods and the predicted values were obtained from the Raman spectra using the chemometric model described in Example One. Included in the plot are the predicted flash point values for 5 unknown fuel samples using a second Raman spectrometer that employed laser excitation shifted from the original spectrometer (large open squares), and the predicted flash point values after the Raman x-axis has been corrected (circles).

The Raman spectra of five jet fuel samples, not contained in the model data set, were measured using the same portable Raman spectrometer and measurement conditions (i.e., laser power, resolution and acquisition time). The correlation model was used to predict the flash point values for the five samples. The values in fact correspond closely to those obtained using the standard tests (FIG. 2, circles).

Figure 3:
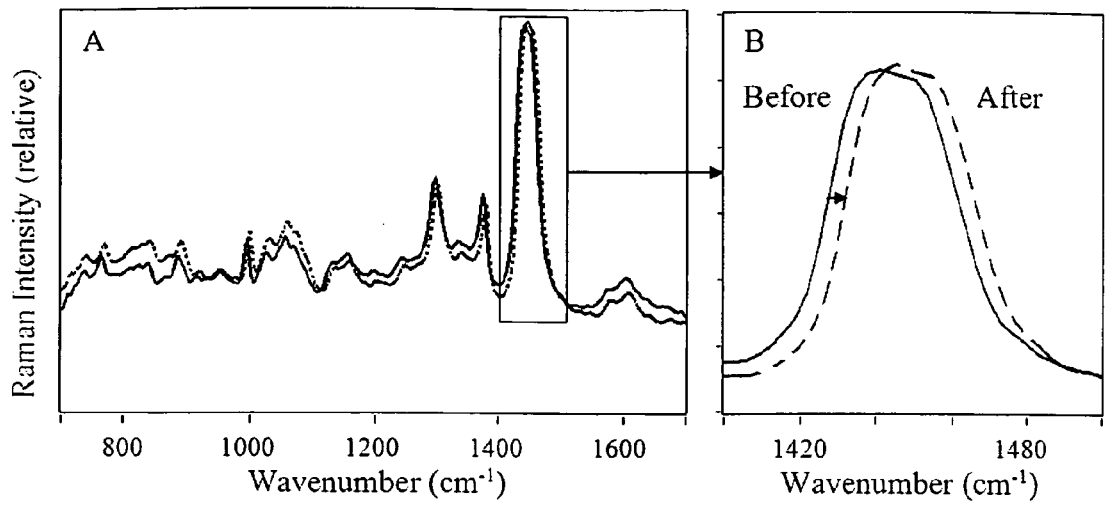
FIG. 3 is a plot of curves (Raman spectra) of one of the unknown fuel samples described in Example One and mentioned in FIG. 1 before and after Raman x-axis correction (4 $cm^{-1}$ shift), showing A) the primary spectral analysis region and B) an expanded view of the 1400 $cm^{-1}$ region to illustrate the x-axis shift performed.

A second FT-Raman spectrometer, i.e. not the one used to measure the original samples used to build the model, was used to obtain Raman spectra of the same five jet fuel samples using the same measurement conditions. The flash points for these samples are all predicted high (FIG. 2, squares). It was found that the laser excitation wavelength was 0.5 nm shifted from the FT-Raman spectrometer used to develop the model. By shifting the Raman spectra of the five samples by this amount (~4 $cm^{-1}$ at this wavelength, FIG. 3), the predicted flash point values are dramatically improved and correspond to the values previously obtained (FIG. 2, circles). Note that only the predicted values change (shift down), while the measured values are of course the same.

Similar to this Raman x-axis shift correction, it is also useful to apply a Raman y-axis correaction to take into account any differences between the Raman spectrometer used to build the original model and the one used to measure the present samples. This spectral intensity correction is accomplished by applying the spectral response function for the measuring instrument to the spectra, just as was done for the original spectrometer. A spectral response function is the sum total of the spectral response for all optics within the instrument, as well as the detector and electronics over the range that the Raman spectra are measured.

Example Two

Figure 4:
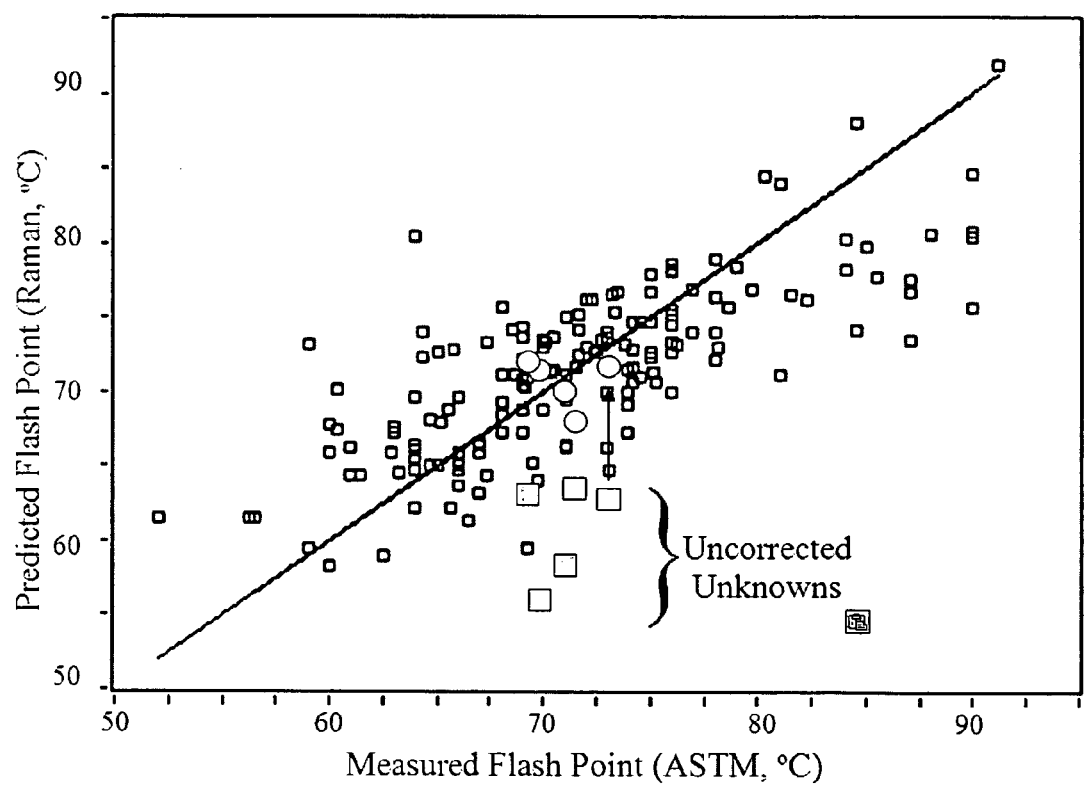
FIG. 4 is a plot of measured versus predicted flash point values for 180 diesel fuels (open squares). The measured values were obtained by standard ASTM methods and the predicted values were obtained from the Raman spectra using the chemometric model described in Example Two. Included in the plot are the predicted flash point values for 5 unknown fuel samples measured at −32° C., uncorrected (large open squares), and corrected (circles) using a set of weighted spectral regions.
Figure 5:
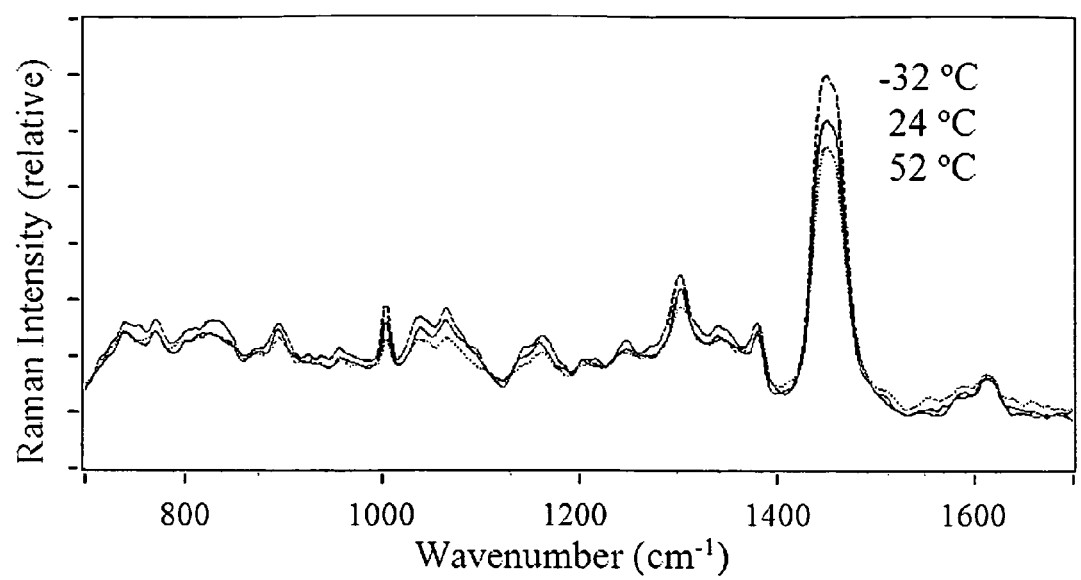
FIG. 5 is a plot of curves (primary Raman spectral analysis region) of one of the unknown fuel samples described in Example Two and mentioned in FIG. 3 measured at −32, 24, +52° C. (top to bottom).

The flash points for 180 diesel fuels were also determined according to the ASTM D93 method, which has a standard deviation of 5.8° C. for this fuel class. The Raman spectra were recorded for these samples using the measurement conditions described in Example One, and a correlation model between the measured Raman spectra and flash points was developed (FIG. 4). The $R^2$ error for the fit to the data is 0.68 and the standard error of prediction for this data set is 4.83° C. Five diesel fuel samples, not contained in the model data set, were measured by Raman spectroscopy as described above, and the diesel correlation model was used to predict their corresponding flash point values with reasonable accuracy (FIG. 4, circles). The same samples were again measured by Raman spectroscopy, but instead at temperatures of −32 and +52° C. (thermo-couple reading of the sample), and are found to have slightly different Raman spectra from those obtained from room temperature samples, defined as 24° C. (FIG. 5). Application of the correlation model predicts low flash point values for the −32° C. samples and high for the +52° C. samples (FIG. 4, large squares, only −32° C. samples shown). The Raman spectra for 36 of the 180 original diesel fuel samples are measured at −32° C. to develop a flash point correlation model for this temperature. Comparison to the room temperature model reveals that the difference between the models is the amount of weighting applied to the spectral regions that are used to correlate to the flash point. Application of a spectral set of factors representing the difference between the weightings of the two models to the −32° C. sample spectra predict flash point values near identical to that obtained from the room temperature spectral data and model (FIG. 4, circles). It is also found that a complete temperature depended Raman-to-flash point correlation model can be developed by measuring similar subsets at modest temperature intervals between −32 to 52° C., such as 14° C. However, each temperature requires a distinct spectral set of factors for the weighted region, or spectral correction factors. It is further found that these spectral correction factors can be plotted as a function of temperature and fit with higher order polynomial equations produce a refined model that allows accurate prediction of flash points from Raman spectra for any temperature within the −32 to +52° C. range, provided the sample temperature is known.

From the foregoing example, it is clear that the present invention can be extended to evaluate the condition of lubricating oils used in vehicle engines and hydraulic fluids used in control systems (e.g. aircraft steering mechanisms). Such oils and fluids degrade over time, which is reflected in a decreasing viscosity value. A model developed using a series of oils or fluids having a range of viscosities, due to natural or intentional degradation, can be used to develop a correlation between the measured viscosity by ASTM methods and the predicted viscosity from Raman spectra. Furthermore, a refined model that includes lubricating oils and hydraulic fluids at various temperatures, so that a fiber optic Raman probe could be used much like a dipstick to determine viscosity while still in an engine block or a control system.

As indicated by this example, the present invention could also be used to determine the thermal stability of jet fuels. Similarly to lubricating oils and hydraulic fluids, jet fuel degrades over time due to thermal and oxidative processes and their combination. The thermal stability of a jet fuel is determined using a Jet Fuel Thermal Oxidation Tester (ASTM D3241) and reporting the breakpoint temperature, the temperature at which there is a pressure drop as the heated fuel passes through a filter. Again, a model can be developed that correlates the Raman spectra to thermal stability, so that the spectrum of a sample can be used to predict the thermal stability in terms of the breakdown temperature, and qualify the fuel for use.

Example Three

Figure 6:
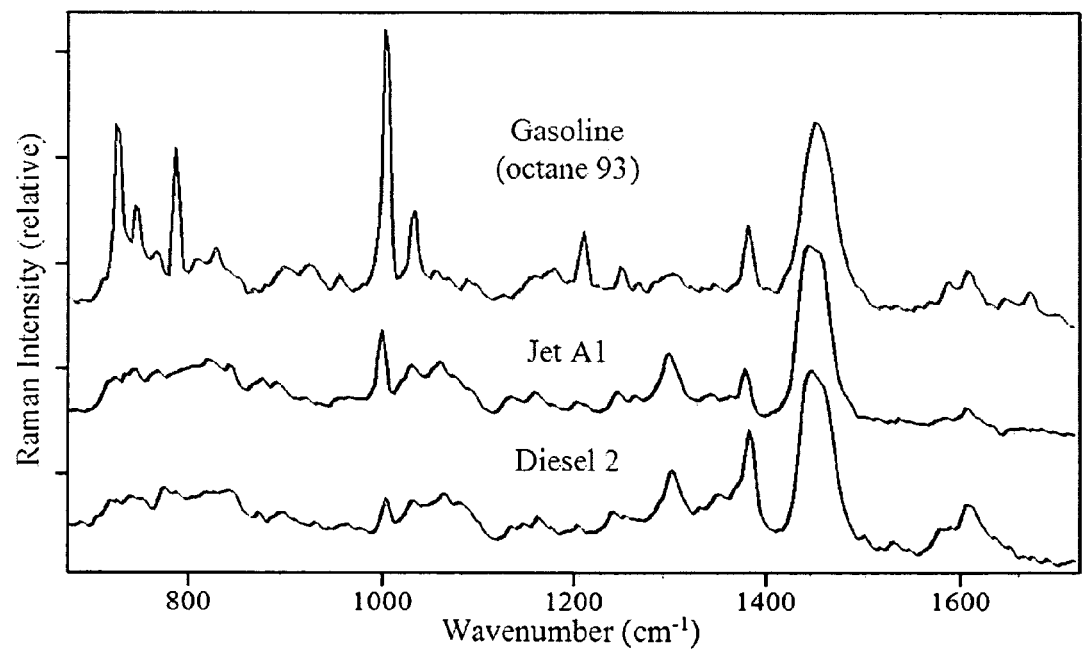
FIG. 6 is a plot of curves showing the primary Raman spectral analysis region for gasoline, jet, and diesel fuels.

It is sometimes important to classify samples of unknown fuels, or even determine the grade of fuel within a class. This can be determined by measuring all of the appropriate properties, chemical, chemical-based, and physical, that define each fuel class and grade. For example, the high aromatic content of gasoline allows it to be differentiated from jet or diesel fuel, while the latter two fuels can be differentiated based on their flash point values. Specifically, if the flash point is below 60° C. it is likely a jet fuel, while above 60° C. it is likely a diesel fuel (see FIG. 2 and FIG. 4). This can also be accomplished by measuring the Raman spectrum of the sample. Aromatic organic chemicals produce two Raman peaks at ~1000 and 1380 $cm^{-1}$, corresponding to single and double-ringed groups. The former peak is very intense in the Raman spectra of gasoline, and it can be used to differentiate this class of fuel from the others (FIG. 6). While the present invention can be used to predict the flash point from the Raman spectrum, and depending if the flash point is higher or lower than 60° C., it can be used to determine if the sample is a diesel or jet fuel.

Figure 7:
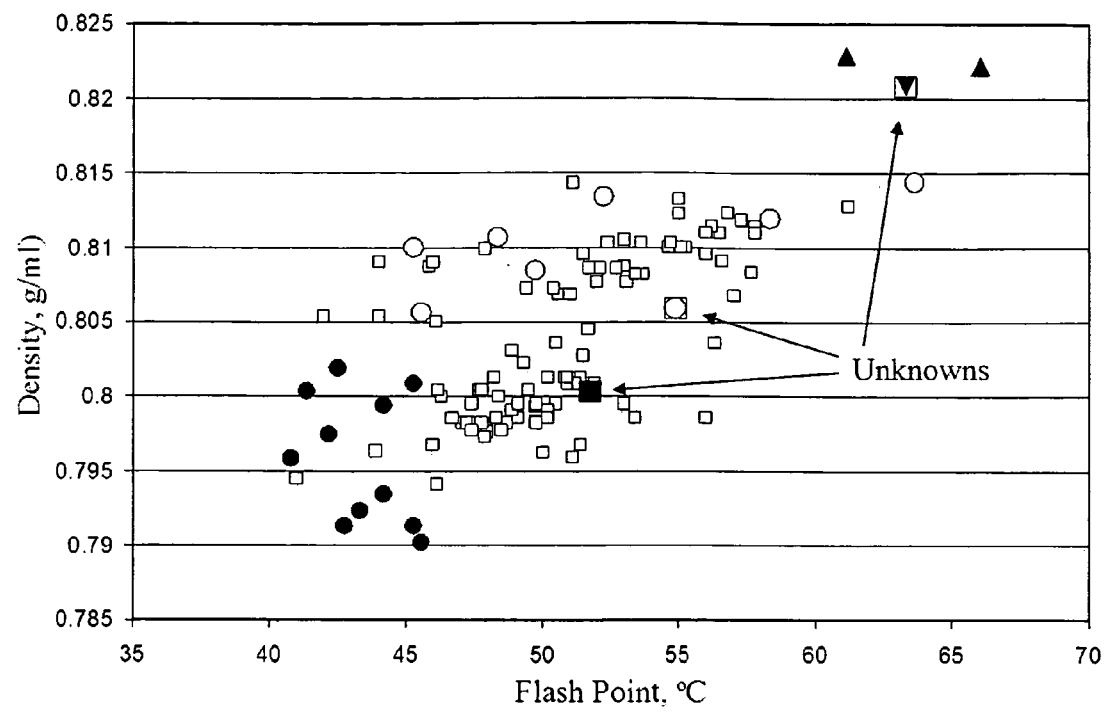
FIG. 7 is a plot of flash point versus density values for 80 jet fuel samples, consisting of Jet A (circles), Jet A 1 (solid circles), JP-5 (triangles), and JP-8 (squares). Three unknown fuel samples are also included and indicated.
Figure 8:
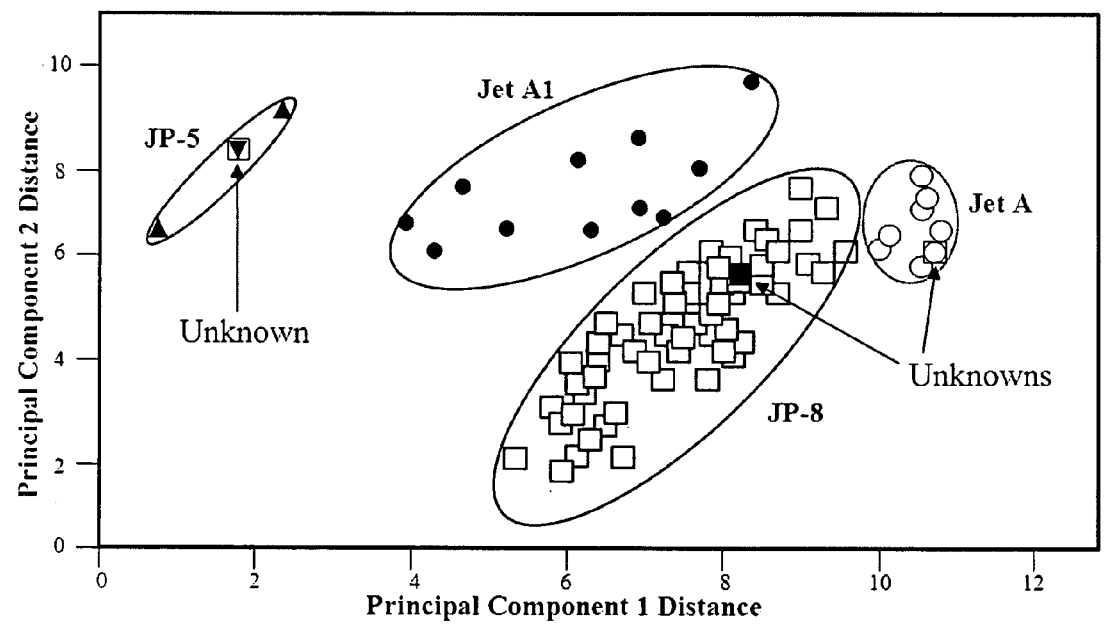
FIG. 8 is a plot of the individual principle components for each of the same 80 jet fuels of FIG. 7 compared (in terms of PC 1 and PC 2 distances) to a unique principal component that has been identified for each grade. The different fuel grades cluster together as indicated by enclosed circles for Jet A (circles), Jet A1 (solid circles), JP-5 (triangles), and JP-8 (squares). The figure also contains three unknowns, represented by a solid square, and a triangle and circle enclosed by an open square, which were identified in terms of fuel grade employing their Raman spectra and the classification model of the present invention.

However, to further determine the fuel by grade, such as differentiating Jet A from Jet A1 or JP-5, requires the inclusion of additional predicted properties. For example a plot of flash point versus density (measured by ASTM or predicted by Raman) for 80 jet fuel samples results in clustering by grade. Both flash point and density values increase in order from Jet A1, Jet A, to JP-5 (FIG. 7, solid circles, shaded circles, and triangles, respectively). However, JP-8 does not separate into a distinct cluster using these two properties (FIG. 7, squares). This is not surprising since, compositionally, it is either Jet A1 or Jet A with specific chemicals added to modify its properties so the fuel is suitable for use in military equipment. However, if additional properties are used to produce an n-dimensional plot of n properties, it can be shown that each jet fuel grade will cluster into separate groups. Alternatively, a classification model can be developed that directly correlates the Raman spectra to the fuel class and grade, just as was developed for the fuel properties. Any of a number of discriminate analysis methods, such as the one previously described, can be used. The Raman spectra for all of the spectra within each jet fuel grade can be averaged and used to determine the principal components that uniquely define each grade. This method was applied to the 80 Jet A, A1, JP-5 and JP-8 samples, and a plot of the distance of each fuel sample from the average results in a clustering of the distances for each fuel grade (FIG. 8).

The Raman spectrum of an unknown sample is collected, and analyzed in accordance with the foregoing coarse model procedures. The aromatic content is much too low to be a gasoline and the sample is more likely a diesel of jet fuel. The predicted flash point for an unknown fuel sample is 63° C., suggesting a possible diesel fuel. However, the predicted 50% boiling point is 218° C. and the density is 0.822, both values more typical of jet fuels. These physical properties suggest that the unknown fuel is a JP-5 (FIG. 7, inverted triangle surrounded by square). Moreover, the refined jet grade classification model places the sample unequivocally in the JP-5 cluster (FIG. 8, inverted triangle surrounded by square) with a flash point of 62° C. Similarly, two additional jet samples have predicted density and flash points of 0.806 and 0.801 g/ml and 55.3 and 52.0° C., respectively, based on a coarse model. These values indicate that the samples are either JP-8 or Jet A, but again, the use of the refined jet grade classification model allows positive identification (FIG. 8, filled square and circle surrounded by square, respectively), and more accurate prediction of the properties.

From the present example, it is obvious that after identification of a fuel by class, and even grade, using a coarse classification model, then more refined property models can be used to improve the accuracy of the predicted property values. In fact the classification model and property models can be used in an iterative fashion to improve fuel identification by class and grade, and determination of fuel properties.

Example Four

Pipelines are used to carry the various fuel classes from ports to major cities for distribution. At the point of changeover from one class to another (e.g. gasoline to jet fuel), the fuels mix. The amount of fuel mixing during transit depends on a number of factors including pipe diameter, distance, flow rate, etc. The mixed fuel, known as "transmix fuel," generally has to be reprocessed (e.g. redistilled), which is expensive. Current practices employ grab samples and laboratory analysis, which take 30 minutes or more. Consequently, as much as 1 hour of good fuel could be erroneously separated as part of the transmix. The present invention (involving, for example, Raman spectroscopy and the fuel classification model described), can be used to measure the relative concentrations of the two fuel classes as they change from one to the next, so that the trans-mix fuel can be identified and properly separated. Moreover, since the Raman analyzer can be directly coupled to the pipeline and measurements can be performed every minute, the amount of good fuel erroneously separated as transmix can be substantially reduced.

Figure 9:
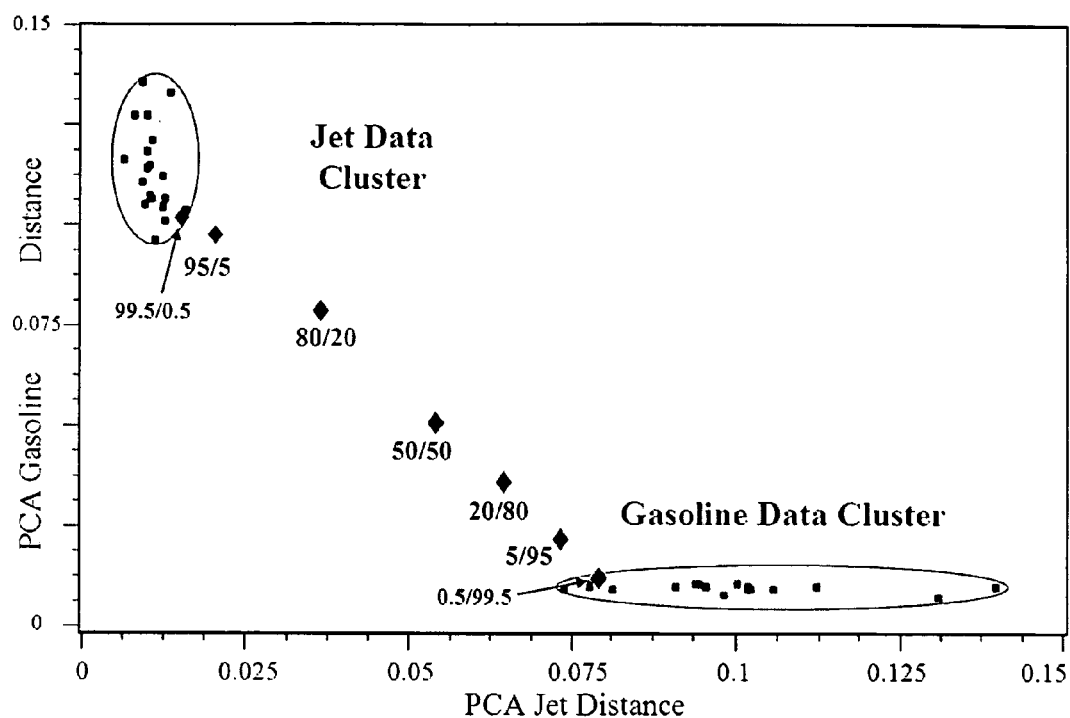
FIG. 9 is also a Principal Component Analysis distance plot which employs the distance between fuel class clusters to quantify the contribution of each class to a fuel sample mixture based on the measured Raman spectra of unknown samples and the classification model of the present invention.

A series of gasoline and jet fuel samples were prepared at various volume percents and measured by Raman spectroscopy. Although, as stated above, the Raman aromatic peak at ~1000 cm$^{-1}$ can be used to distinguish gasoline from jet fuel, quantitative analysis of transmix would require preparing concentration series for every possible gasoline and jet fuel combination. This is particularly true since the intensity of the aromatic peak can change significantly from gasoline to gasoline. Instead, however, a coarse classification model that includes the various gasolines and jet fuels, can be developed and used to calculate the "distance" between the cluster for each class in terms of principal components and a refined model to relate these distances to concentration (FIG. 9, diamonds). The model adequately identifies the composition to within 1 volume percent of one fuel in the other, sufficient to decide transmix separation. This model can then be used to monitor the changeover from one fuel class to another and control the amount of transmix separated into the reprocessing tank. In the present case, the changeover could be defined as the mixture that produces a distance just outside a predefined acceptance statistical confidence level, such as 95%, as suggested previously. In addition to quantifying the changeover based on the classification model, a simple two-component mixture analysis could also be used. However, since there is considerable overlap of the composition of all of the fuel classes and grades, chemometric methods, such as PLS, could be used to develop a further refined model to provide better quantification, once the two fuel classes have been determined by a coarse model.

It should be realized that the same model or models can be used, for example, 1) to determine commingled fuels in fuel trucks, 2) to determine the unintentional contamination of fuel by other petroleum products, 3) to monitor and control the addition of gasoline to jet fuel to produce JP-4 (also known as Jet B), 4) to identify adulteration of fuels by adding less expensive fuels or organics (e.g. naphtha in gasoline), and 5) the intentional sabotage of fuel by the addition of chemicals and explosives.

Example Five

Figure 10:
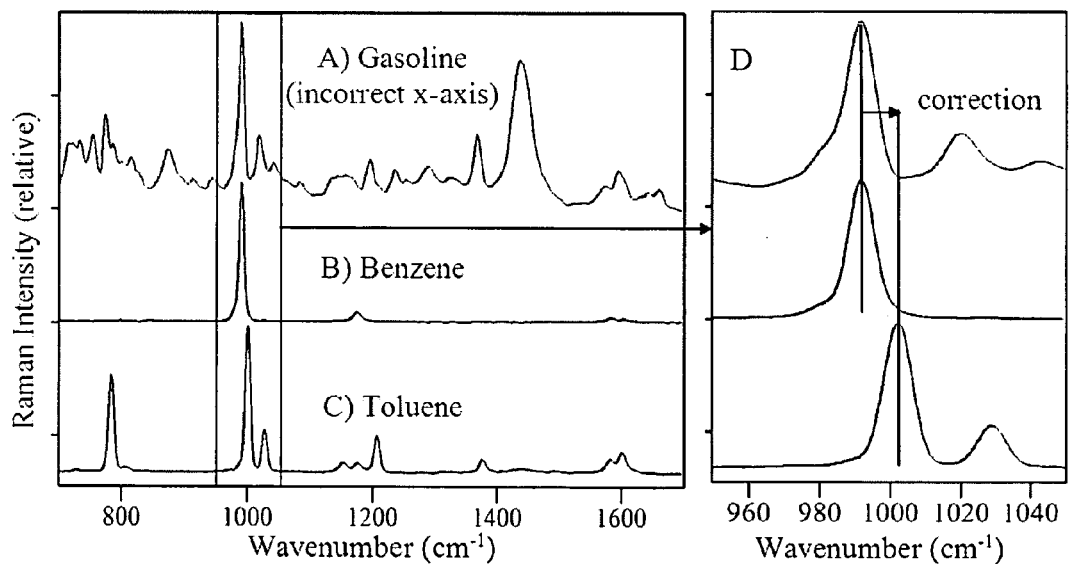
FIG. 10 is a plot of curves showing the primary Raman spectral analysis region for A) Gasoline (displaced x-axis), B) Benzene, and C) Toluene; curve D) is an expanded view of 1000 $cm^{-1}$ peaks, and the shift required to correct the measured spectrum and the analysis.

The general goal of gasoline blending is to match supply to demand for the different gasoline grades based on octane number. In some cases this involves simply mixing a high and low octane rated gasoline to produce an intermediate octane gasoline. In other cases the gasoline "cut" obtained during refining and distillation is below the desired octane value and needs to be increased. This is often accomplished by adding aromatics, particularly the xylenes. Raman spectra can be used to evaluate the initial distillation cut to determine both the amount of aromatics present and the octane value using chemometric models. In the case of the former it is important to know the percent of BTEX since these chemicals are highly regulated and limited to ~35 volume percent. In the particular case of benzene, it is limited to less than 1%. FIG. 10A is a Raman spectrum of distilled gasoline. Raman spectral analysis that employs the Raman peaks near 1000 $cm^{-1}$ to quantify aromatics suggests that the cut is very high in benzene (FIG. 10B) and must be diluted to meet regulations. However, the laser in the analyzer had been recently replaced, and no attempt was made to correct the positioning of the x-axis. Once this ~10 $cm^{-1}$ correaction is made, it is found that the aromatic peak in fact corresponds to toluene (FIG. 10C), not benzene, and no dilution is required. Furthermore, the total aromatic content is below 35% and xylenes can be added. Alternatively, a refined model could be developed to automatically adjust the x-axis based on invariant peaks to achieve the same result.

Example Six

A distillation tower is designed to separate a petroleum fraction having Diesel 2 properties. A final boiling point of 350° C. is typical. A series of production runs is performed at several temperatures ranging from 300 to 400° C. using the same crude oil starting material. Raman spectroscopy and the present invention are used to characterize samples collected at each temperature in terms of chemical, chemical-based, and physical properties. A Raman spectrometer is integrated into the tower using a fiber optic coupled probe to monitor and control not only the chemical composition of the distillate, but also its chemical-based and physical properties. Of course the same approach could be used to control a distillation tower to produce other fuel classes and fuel grades based on the fuel properties determined by the present invention.

Example Seven

Biodiesel is being developed as an alternative fuel to those refined from petroleum products, since it can be produced from renewable sources, such as vegetable oils and animal fats, as well as from wastes, such as used cooking oil. Currently, there is a considerable effort to improve the efficiency of the transesterification reaction used to convert these oils and fasts to biodiesel. Determination of the reaction kinetics and efficiency involve drawing samples and measuring the decrease in triglyceride (oil or fat) and formation of methyl esters (biodiesel fuel). This is most accurately performed using gas chromatography, which requires 30 minutes per sample (ASTM D6584-00).

Figure 11:
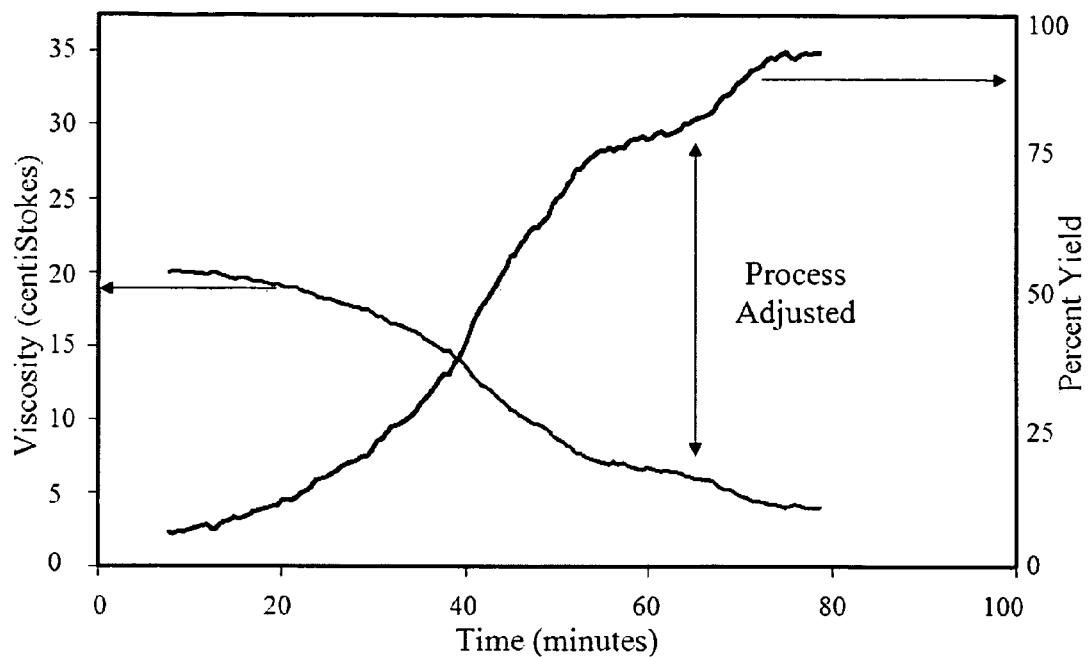
FIG. 11 is a plot of curves showing the viscosity (left y-axis) and percent yield (right y-axis) of a biodiesel reaction as a function of time (x-axis), wherein the Raman spectra measured during the course of the reaction is used to calculate these values using the present invention, monitor the performance of the reactor, and adjust process conditions (addition of catalyst) to optimize performance (yield) and control the final biodiesel product properties.

Similar to the previous example, a biodiesel reactor is designed to convert waste vegetable oil to biodiesel. Chemically, a transesterification reaction is performed in which triglycerides (vegetable oil) are reacted with methanol to form methyl esters (biodiesel fuel) and glycerol as a side product. A similar series of production runs are performed in which the amount of catalyst, such as potassium hydroxide, is changed. Again, the present invention (involving, for example, Raman spectral measurements correlated to fuel properties) is used to characterize samples collected for each catalyst concentration in terms of chemical (e.g. residual triglyceride, ester, and glycerol concentrations), chemical-based (acid number), and physical properties (cloud point, net heat of combustion, and viscosity). As in the previous example, a Raman spectrometer is integrated into the reactor using a fiber optic coupled probe to monitor reaction rates and yield, for the purpose of controlling operating conditions (catalyst loading, temperature, etc.) and product properties. For example, during the course of a reaction, the R—C=O Raman stretching mode at 860 $cm^{-1}$ is used to monitor the percent yield, while the chemometrics analysis of the spectrum is used to monitor the viscosity as a predicted value (FIG. 11). It is noted that the yield has begun to plateau at 75%, lower than normal. But more importantly, the viscosity will not reach the ASTM required value of 6.0 centiStokes. The process is adjusted by adding potassium hydroxide, the amount based on the model, to achieve the desired viscosity and increase the yield. Of course the present invention could also be used to predict the chemical-based and physical properties of the biodiesel product once it has been generated. The present invention could also be adapted to other biofuel reactors, as well as reactors designed to convert renewable sources, such as switch grass and corn stalks into basic chemical feedstocks.

Example Eight

Figure 12:
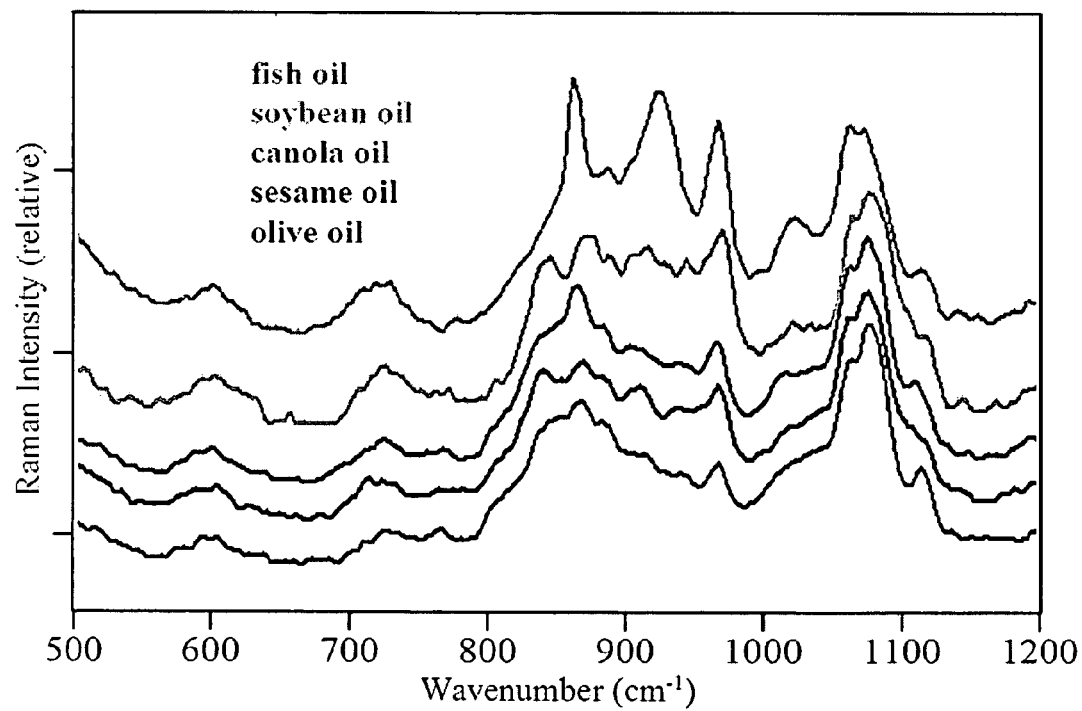
FIG. 12 is a plot of curves showing the primary Raman spectral analysis region for fish, soybean, canola, sesame, and olive oil (top to bottom).
Figure 13:
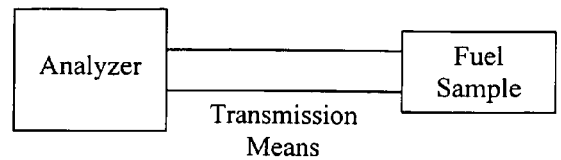
FIG. 13 is a diagrammatic representation of apparatus embodying the present invention and consisting of an analyzer, a fuel sample holder, and transmission means for providing spectral data obtained from a fuel sample to the analyzer. The analyzer includes the means for providing a coarse mathematical model, the means for providing a multiplicity of fine mathematical models, the means for performing a coarse analysis of an obtained spectrum, and the means for performing a fine analysis of the spectrum, all as described herein.

The present invention could also be used to select the process conditions that optimize both energy use and yield based on Raman spectra of the feedstock to be used in a biodiesel reactor. The exact triglyceride composition of this starting material is different from one source to another. In the case of vegetable oil feedstocks, each triglyceride molecule contains three fatty acids (saturated and unsaturated). The relative amount of these acids, such as butyric, linoleic, oleic, palmitic, stearic, etc., differ from canola, corn, fish, sesame, soybean, olive, and other oils. The fatty acid composition of these feedstocks is typically determined by a combination of gas chromatography and mass spectrometry. This technique requires constant calibration, is labor intensive, and takes as much as an hour to perform. The present invention could be used to build a model correlating the Raman spectra of the starting materials (see FIG. 12) to the reactor process conditions that produce the highest yield. Specifically, a feedstock oil high in linolenic acid (18-carbon chain) may require significantly more heat (higher process temperature and longer reaction time) than a feedstock oil high in butyric acid (4-carbon chain). The more practical use of the model, in a refined form, would allow selecting the optimum process conditions for mixed feedstock oils, as well waste oils used as feedstocks that have experienced a range of heat conditions (e.g. amount of time a frying oil is heated and cooled), based on a 1-minute Raman spectrum of the starting material.

As will be appreciated, the database used in the method of the invention will normally include properties and spectra of fuel samples measured at multiple sample, instrument, and ambient temperatures, wherein the sample temperature is the temperature of the sample at the time of measurement and the ambient temperature is the temperature outside the sample. The temperature measurements should be sufficient in number to employ the models to predict fuel properties at the measured temperatures and at intermediate temperatures. The model employs sample, instrument, and ambient temperature information to select the appropriate temperature database, and determines properties of a measured sample, at a given ambient, instrument, and sample temperature, by using the corresponding temperature database. The model should also be capable of determining property values of a measured sample at a given ambient, instrument, and sample temperature that does not correspond to a temperature in the database by interpolating each property value from the predicted property values for temperatures above and below the given temperature. The interpolated value may for example be half the sum of the two values, each multiplied by the difference between the corresponding temperatures above and below the given temperature. Alternatively, the interpolated value may be a value determined by fitting the values for a given property at every measured temperature in the database with a polynomial equation, and using the equation to determine the property value at the given temperature. As a further alternative, the model may determine property values of a measured sample at a given ambient and sample temperature, that does not correspond to a temperature in the database, by interpolating a factor from the factors used to weight the spectral regions at temperatures above and below the given temperature for each of the spectral regions used to correlate to a given property.

Temperature measurements will generally be made at intervals of 20° C. or smaller; preferably, the intervals will be 14°, and more desirably they will be 5°. The measured and ambient temperatures will usually be between 0 and 40° C. (32 to +104° F.), and preferably between −32 to +52° C. (−25 to +125° F.).

Linear regression models employed in the method may include principal component analysis, principal component regression analysis, partial least squares, classical least squares, inverse least squares, or other models known to those skilled in the art. Separate regression models can be used for each property, to optimize the prediction or determination of the property for an unknown sample, and can be used for each fuel class and grade to optimize the prediction or determination of the property for an unknown sample. Regression models can be optimized by using one or more selected spectra ranges. The model may employ the spectra of fuel samples within a given class or grade to determine a regression component that uniquely defines that fuel class or grade, so that it can be differentiated from other fuel classes and grades, and statistical confidence levels (such as 90, 95, and 99 percent) are desirably used to determine if a sample is a member of a fuel class or grade; conversely, statistical confidence levels (such as 10, 5 and 1 percent) may desirably be used to determine if a sample does not belong to a fuel class or grade. The distance that the regression component of a given fuel sample is from the regression component that defines the fuel in terms of class or grade is calculated using mathematical algorithms, such as Absolute Value, Correlation, Euclidean, Least Squares, and Mahalanobis distance algorithms.

As will of course be appreciated, the models employed in the present method and apparatus allow an unknown fuel to be classified in terms of class and grade so that models specific to that class and grade can be used to best predict and evaluate properties. The models employ a general fuel correlation model to determine general fuel properties, then classify the fuel based on the determined properties, and thereafter select the models specific to that fuel grade, so as to refine the determination of fuel properties, iteratively. The mathematical model preferably employs methods to pre-treat (preprocess) the spectra, such as by y-axis and x-axis adjustments. Thus, y-axis adjustments include methods to adjust the baseline of the spectra and normalize the spectral intensity, such as by removing tilt and/or curvature in the baseline by fitting the baseline with polynomial or exponential equations and then subtracting the fit from the spectrum, or subtracting a spectral response function, or employing multiplicative scatter corrections, to determine the average value that the baseline should have. Normalization methods include setting the baseline to zero and the most intense peak to 1, taking the first, second, or higher derivative of the spectrum, or applying mean-centered or maximum value normalization.

Adjustments to the x-axis include methods to shift spectra so that all spectra and samples have the same x-axis. Such shift methods include measuring the laser excitation frequency and shifting the spectra so that its value is zero wavenumbers, measuring a Raman peak that is invariant to properties, and shifting the spectra so that this value is at its known wavenumber. Such an invariant Raman peak is preferably the $CH_2$ wagging mode that appears at 1450 $cm^{-1}$ in the Raman spectra of fuels. In addition, pre-treatment may also include methods to reduce the noise contribution to the spectra, such as moving average, Savitsky-Golay, Fourier transform filtering, etc.

Although fluorescence, laser induced breakdown, infrared, near infrared, and terahertz spectrometers can be employed in the practice of the invention, in many instances a Raman spectrometer, and especially Raman spectrometer that employs an interferometer to separate the component wavelengths, will be preferred. The spectrometer may employ laser excitation at an ultraviolet, visible, near infrared or infrared wavelength. Preferably however the laser wavelength will be longer than 800 nm, more preferably 976 nm, and most desirably 1064 nm. Laser power in the spectrometer will desirably be 2 W or less, and the spectral acquisition time will be preferably 5 minutes or less and most desirably 1 minute or less. The spectrometer should be capable of operating at temperatures between 0 and 40° C. (32 to +104° F.), and preferably it will operate effectively at temperatures between −32 to +52° C. (−25 to +125° F.).

As indicated above, the spectrometer will advantageously be portable, and should be sealed so that liquids, sand, and the like can not enter the apparatus; i.e., it should be adapted to operate in rain and in under wind-blown sand conditions. The optical interface of the spectrometer will of course permit the excitation laser to be directed into the sample, and the scattered Raman energy to be collected. Preferably, the transmission means (i.e., the optical interface) will be a focusing lens, or a focusing lens in combination with an optical window, and it may be incorporated into a sample compartment or be a fiber optic-coupled probe. The sample compartment may be designed to hold capillaries, cups, pipettes, test tubes, vials, and other implements that may hold or contain fuel; it will be appreciated that the apparatus may be built to accommodate an inserted sample holder, with the spectral data transmission means and the analyzer being integrated in a common housing. Alternatively, a fiber optic-coupled probe, designed as a dip probe for measuring fuel in storage tanks and vehicle tanks, may be employed; more particularly, a fiber optic-coupled probe may for example be designed to interface to fuel pipelines, distillation columns, petroleum fractionation towers, reactors, or other equipment that may hold, contain or be used to process fuels. Both a sample compartment and also a probe may include a thermocouple, a thermometer, a thermister, a pyrometer, etc. to monitor and transmit temperature data.

Thus, it can be seen that the present invention provides a method and apparatus that enable identifying unknown fuels by class and grade, determining properties of unknown fuels, identifying and quantifying mixed fuel classes (such as commingled fuels in trucks or pipelines), identifying fuels that that are not within specifications based on determined properties, and identifying additives, contaminants, or adulterants in such fuels. The invention also enables monitoring and controlling of the blending of fuels, such as gasolines, to achieve a desired octane rating, monitoring and controlling of distillation towers to selectively distill and collect a specific fuel class or grade, monitoring and controlling of reactors used to synthesize fuels, such as for optimizing yield and properties of biodiesel made from food oils, selecting process conditions based on raw material properties, etc.

Having thus described the invention, what is claimed is:

1. A method for determining spectroscopically the value of at least one property of a fuel sample of unknown character, comprising:

providing a coarse mathematical model, created using a database, in which either or both of (a) the nature and values of characteristics that are indicative of fuels of at least two classes, or (b) one or more spectral representations of the nature and values of characteristics that are indicative of fuels of said at least two classes, taken cumulatively, at temperatures over a range of common values, are correlated to measured spectra in a selected spectral range, said fuel characteristics including, directly or indirectly, chemical functional groups and a plurality of properties;

providing a multiplicity of fine mathematical models, created independently using said database, in each of which a plurality of spectral components are correlated to a property of fuels within each of said at least two classes, such correlations being based upon either or both of (a) the nature and value of fuel characteristics, or (b) one or more spectral representations of such characteristics, taken cumulatively and at temperatures over said range of common values, separate pluralities of said multiplicity of fine mathematical models being grouped together so as to provide at least a first multiplicity of fine model groups, a first plurality of said first multiplicity of fine model groups being peculiar to fuels within at least a first one of said two classes, and a second plurality of said first multiplicity of fine model groups being peculiar to fuels within at least a second one of said two classes;

obtaining, through measurements, a spectrum, within said spectral range, of a fuel sample of unknown character, at least at one temperature within said range of common values;

performing a coarse analysis of said obtained spectrum by comparing said obtained spectrum to said measured spectra, using said coarse mathematical model, so as to identify a class to which the fuel of said sample belongs; and performing a fine analysis of said obtained spectrum by comparing said obtained spectrum to said measured spectra, using said first plurality of fine model groups if said class to which said fuel sample belongs is determined, by said course analysis, to be said first one of said two classes, or using said second plurality of fine model groups if said class to which said fuel sample belongs is determined, by said coarse analysis, to be said second one of said two classes, so as to thereby determine a value for said correlated property of said fuel of said sample.

2. The method of claim 1 wherein, in said coarse model, characteristics that are indicative of fuels of a variety of classes are so correlated to said measured spectra, said variety of classes including gasolines, diesel fuels, biodiesel fuels, and aviation fuels.

3. The method of claim 2 wherein said fuels of said variety of classes are of different grades, and are selected from the group consisting of gasoline octane grades, oxygenated gasolines, diesel 1, diesel 2, Jet A, Jet A1, JP-4, JP-5, JP-7, JP-8, biodiesel 20, biodiesel 50, and biodiesel 100.

4. The method of claim 1 wherein each of said mathematical models comprises at least one weighted spectral region created from said database.

5. The method of claim 1 wherein said database is constructed by measurement of at least 100 different fuels.

6. The method of claim 1 wherein said temperatures over said range of common values are selected from sample temperatures, instrument temperatures, ambient temperatures, and combinations thereof, and wherein said range of common values is −32° to 52° Centigrade.

7. The method of claim 6 wherein said measured spectra are measured at temperature increments of not greater than 20 Centigrade degrees.

8. The method of claim 1 wherein said properties of said plurality of properties are selected from the group consisting of chemical, chemical-based, and physical properties.

9. The method of claim 8 wherein said properties are chemical properties selected from the group consisting of acid, alcohol, aldehyde, alkane, alkene, aromatic, base, biphenyl, ester, ether, glycol, naphthene, phenyl, sulfur, triglyceride and water.

10. The method of claim 8 wherein said properties are chemical-based properties selected from the group consisting of octane number, cetane number, and Reid vapor pressure.

11. The method of claim 8, wherein said properties are physical properties selected from the group consisting of flash point, viscosity, density, net heat of combustion, cloud point, pour point, boiling point, freezing point, lubricity, thermal stability, and initial, final, and intermediate distillation temperatures.

12. The method of claim 1 wherein said obtained spectrum is selected from the group consisting of Raman, infrared, and near-infrared spectra.

13. The method of claim 12 wherein the x-axis of said obtained spectrum is adjusted so as to cause the major peaks thereof to substantially match the major peaks of spectra in said database.

14. Apparatus for determining, spectroscopically, the properties of a fuel sample of unknown character, comprising:

an analyzer having means providing a coarse mathematical model, created using a database, in which either or both of (a) the nature and values of characteristics that are indicative of fuels of at least two classes, or (b) one or more spectral representations of the nature and values of characteristics that are indicative of fuels of said at least two classes, taken cumulatively, at temperatures over a range of common values, are correlated to measured spectra in a selected spectral range, said fuel characteristics including, directly or indirectly, chemical functional groups and a plurality of properties; means providing a multiplicity of fine mathematical models, created independently using said database, in each of which a plurality of spectral components are correlated to a property of fuels within each of said at least two classes, such correlations being based upon either or both of (a) the nature and value of fuel characteristics, or (b) one or more spectral representations of such characteristics, taken cumulatively and at temperatures over said range of common values, separate pluralities of said multiplicity of fine mathematical models being grouped together so as to provide at least a first multiplicity of fine model groups, a first plurality of said first multiplicity of fine model groups being peculiar to fuels within at least a first one of said two classes, and a second plurality of said first multiplicity of fine model groups being peculiar to fuels within at least a second one of said two classes; means for performing a coarse analysis of an obtained spectrum by comparing the obtained spectrum to said measured spectra, using said coarse mathematical model, so as to identify a class to which the fuel of the sample belongs; and means for performing a fine analysis of the obtained spectrum by comparing the obtained spectrum to said measured spectra, using said first plurality of fine model groups if the class to which said fuel sample belongs is determined, by said course analysis, to be said first one of said two classes, or using said second plurality of fine model groups if said class to which said fuel sample belongs is determined, by said coarse analysis, to be said second one of said two classes, so as to thereby determine a value for said correlated property of said fuel of said sample; and transmission means for providing spectral data obtained from a fuel sample to said analyzer.

15. The apparatus of claim 14 wherein said analyzer is selected from the group consisting of Raman, infrared, and near-infrared spectrometers.

16. The apparatus of claim 15 wherein said apparatus is portable, and additionally includes temperature-measuring means for determining at least one of ambient temperature, instrument temperature, and sample temperature, said temperature-measuring means being selected from the group consisting of thermocouples, thermometers, thermisters, pyrometers, and combinations thereof.

17. A method for determining spectroscopically a value for at least one property of a fuel sample of unknown character, comprising:

providing a coarse mathematical model, created using a database, that is capable of determining the class, among a multiplicity of classes, to which a fuel sample of unknown character belongs, in which coarse model either or both of (a) the nature and values of characteristics that are common to fuels belonging to each of a multiplicity of fuel classes and are distinguishing of fuels of other fuel classes, and (b) one or more spectral representations of such characteristics, the nature and values and the spectral representations being taken cumulatively and at temperatures over a range of common values, are correlated to measured spectra in a selected spectral range, said fuel characteristics including, directly or indirectly, chemical functional groups and a plurality of properties;

providing a multiplicity of fine mathematical models, created independently using said database, each of said fine models having a plurality of spectral components that correlate to a property of specific interest in fuels belonging to at least one of each of said multiplicity of classes, said correlations being based upon either or both of (a) the nature and value of fuel characteristics and (b) one or more spectral representations of such characteristics, taken cumulatively and at temperatures over said range of common values;

obtaining, through measurements, a spectrum, within said spectral range, of a fuel sample of unknown character, at least at one temperature within said range of common values;

performing a general analysis of said obtained spectrum by comparing said obtained spectrum to said measured spectra, using said coarse mathematical model, so as to determine the class, among said multiplicity of classes, to which the fuel of said sample belongs and to thereby enable selection of at least one specific mathematical model that correlates to a property of interest in said fuel of said sample, as belonging to said class determined; and performing a fine analysis of said obtained spectrum, by comparing said obtained spectrum to said measured spectra, using at least one selected specific fine model that corresponds to a property of interest in fuels of the class so determined by said coarse analysis, so as to thereby determine a value for said property of interest of said fuel of said sample.

* * * * *